United States Patent [19]

Hirano et al.

[11] Patent Number: 4,463,425
[45] Date of Patent: Jul. 31, 1984

[54] PERIOD MEASUREMENT SYSTEM

[75] Inventors: Toshinori Hirano; Masakazu Murase, both of Fujinomiya, Japan

[73] Assignee: Terumo Corporation, Tokyo, Japan

[21] Appl. No.: 281,163

[22] Filed: Jul. 7, 1981

[30] Foreign Application Priority Data

Jul. 17, 1980 [JP] Japan ................................. 55-97820
Jul. 17, 1980 [JP] Japan ................................. 55-97821

[51] Int. Cl.³ .......................................... G01R 23/02
[52] U.S. Cl. ..................................... 364/417; 364/487; 128/704
[58] Field of Search ................. 364/417, 487; 128/698, 128/704, 706, 708

[56] References Cited

U.S. PATENT DOCUMENTS 4,037,151  7/1977  Takeuchi .................... 128/698 X
4,054,862 10/1977  Backman, Jr. ............... 343/100 CL
4,239,048 12/1980  Steuer ............................ 364/417 X

FOREIGN PATENT DOCUMENTS 2546856  5/1976  Fed. Rep. of Germany.
2818768 11/1979  Fed. Rep. of Germany ...... 364/417

OTHER PUBLICATIONS

IEEE Transactions on Bio-Medical Engineering, vol. BME-15, No. 1, Jan. 1968, New York, (US), J. H. Van Bemmel, "Detection of Weak Foetal Electrocardiograms by Autocorrelation and Crosscorrelation of Envelopes", pp. 17 to 23.
IEEE Transactions on Bio-Medical Engineering, vol. BME-13, No. 1, Jan. 1966, New York, (US), A. G. Favret et al., "Evaluation of Autocorrelation Techniques for Detection of the Fetal Electrocardiogram", pp. 37 to 43.
IEEE Proceedings A, vol. 128, No. 8, Nov. 1971, Hitchin Herts, (GB), C. H. Sande et al., "Aid to Diagnoisis of Foetal Bradicardias Using the Autocorrelation Function", pp. 571 to 575.
Takeuchi, Y. and Hogaki, M., "An Adaptive Correlation Ratemeter: A New Method for Doppler Fetal Heart Rate Measurements", *Ultrasonics*, vol. 16, No. 3, pp. 127–137, May 1978.
Clark, J. S. B. and Filshie, J. H., "Autocorrelation Techniques for Measuring Avian Heart Rates", *Med. & Biol. Eng. & Comput.*, vol. 15, pp. 656–665, Nov. 1977.

Primary Examiner—David H. Malzahn
Assistant Examiner—Ronni S. Malamud
Attorney, Agent, or Firm—Frishauf, Holtz, Goodman & Woodward

[57] ABSTRACT

A period measurement system adapted to sample a biosignal at a predetermined sampling period, find an autocorrelation function for a variable τ from the sampled biosignal, and then find an autocorrelation function corresponding to the value of a phase difference variable obtained by changing the variable τ along a time axis. An autocorrelation function found in this manner is stored in memory and then compared with a subsequent-found autocorrelation function. The comparison operation is repeated for successive autocorrelation functions, thereby to find a peak of autocorrelation functions to measure the period of the biosignal.

7 Claims, 9 Drawing Figures

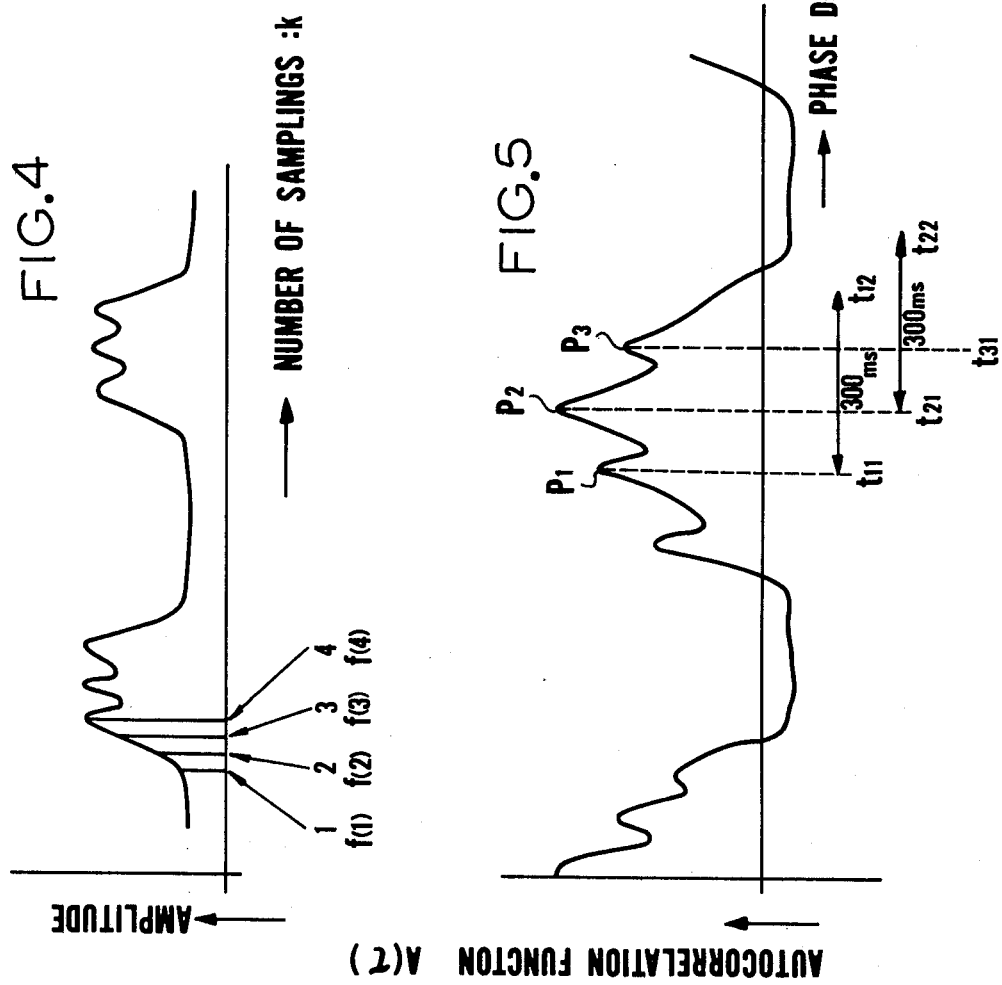

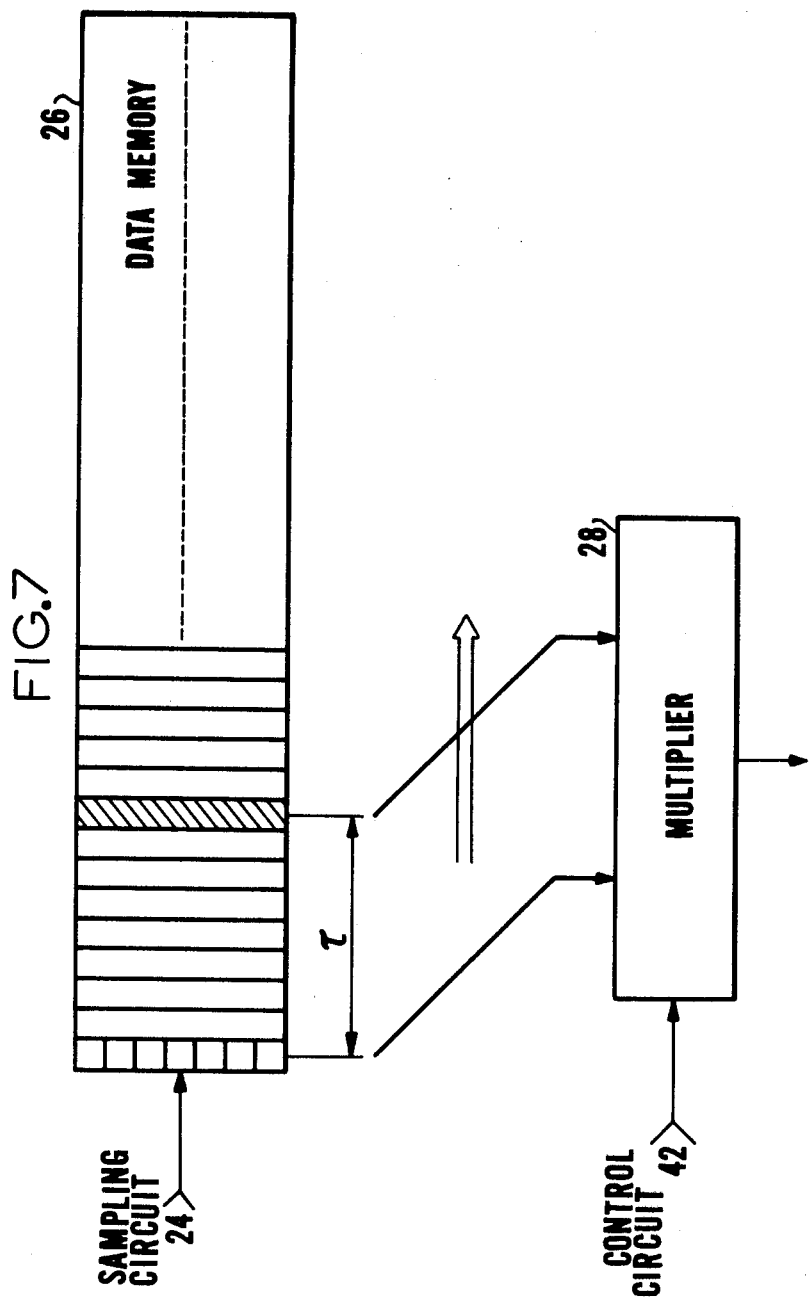

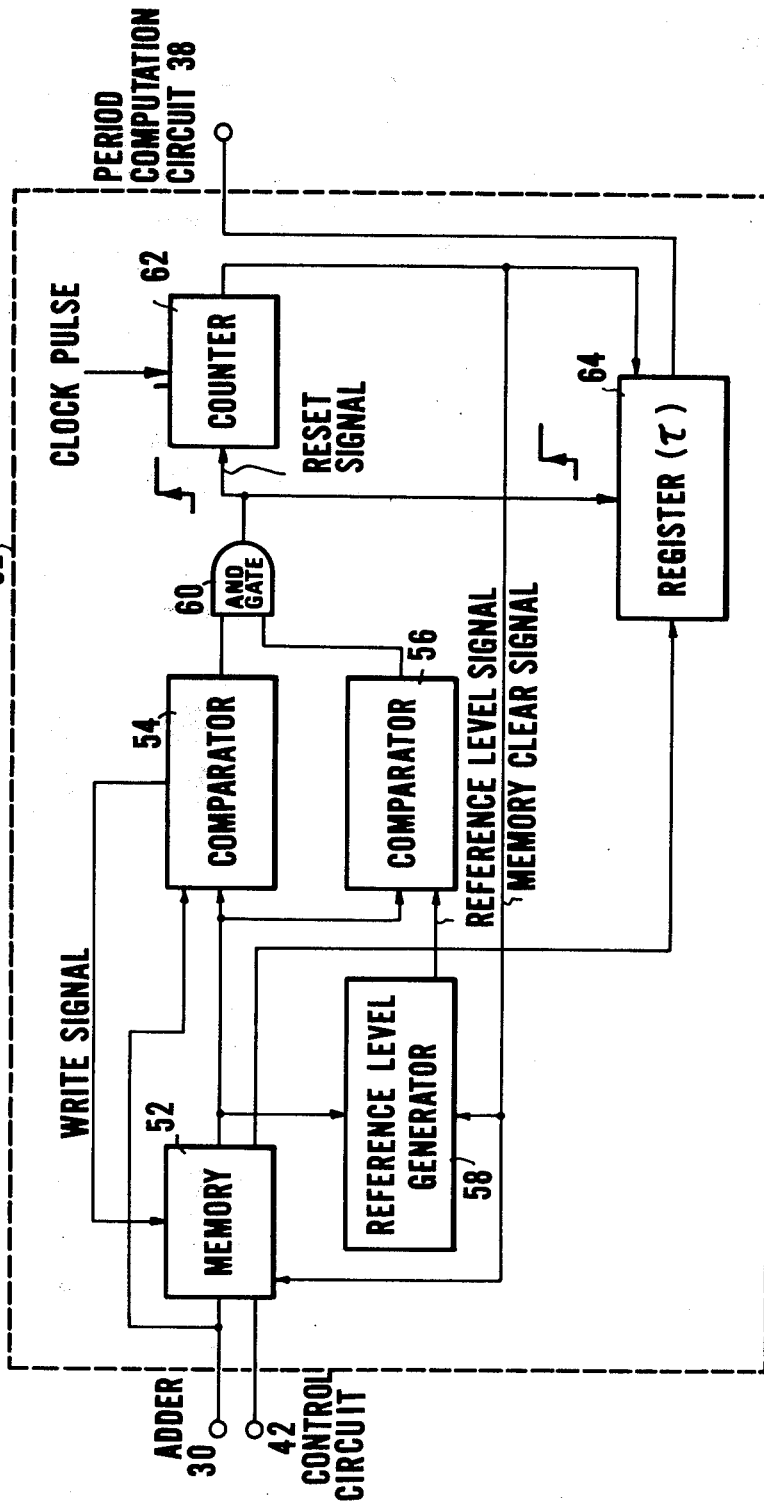

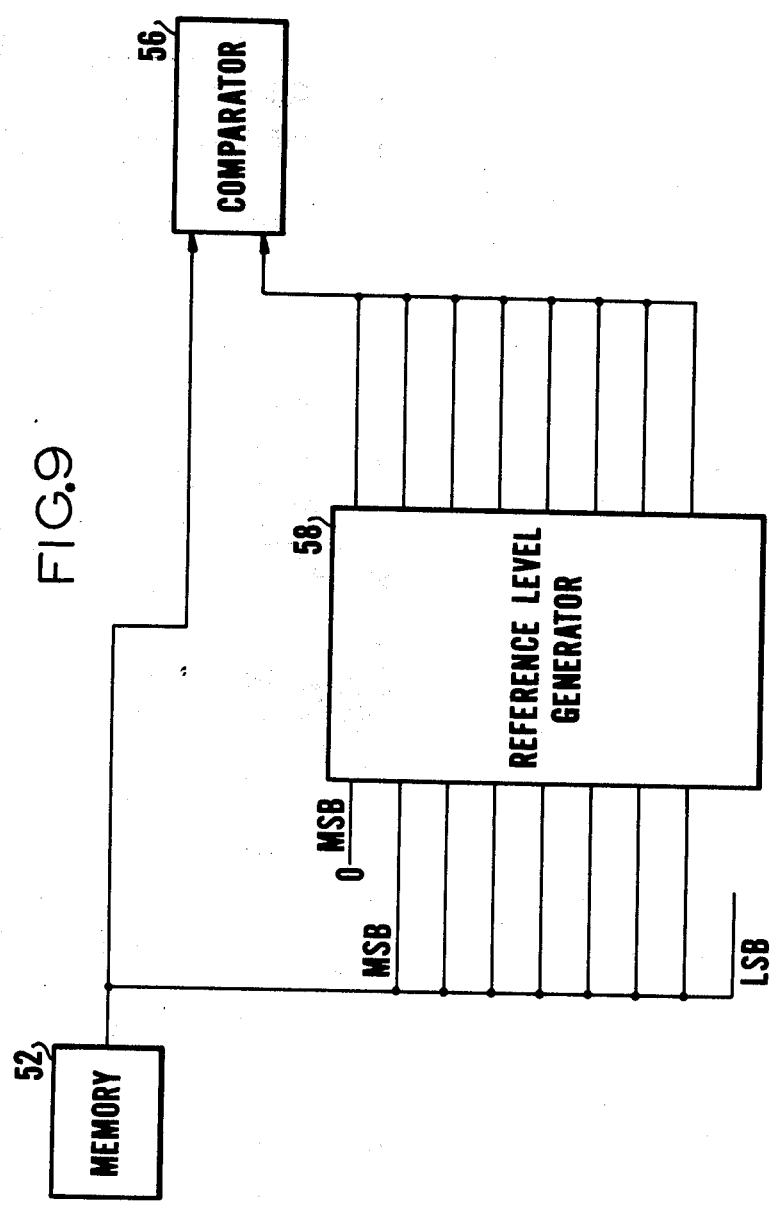

PERIOD MEASUREMENT SYSTEM

BACKGROUND OF THE INVENTION

This invention relates to a period measurement system for measuring the period of a biosignal, particularly of a signal representative of the heartbeat of a fetus.

A conventional system for measuring the period of a biosignal relies upon a correlation system adapted to derive an autocorrelation function of the biosignal, and to measure the period of the biosignal of the basis of the autocorrelation function.

The period measurement system that relies upon the correlation system operates by sampling a biosignal over a suitable sampling period, computing the autocorrelation function of the biosignal from the sampled data, and detecting the peaks of the biosignal from the computed autocorrelation to thereby obtain the period.

The autocorrelation function indicates the similarity between two portions of the biosignal wave form at two different times separated by a certain time interval. In other words, it represents the degree of similarity of the repeating biosignal waveform. This can be better understood from FIG. 1, wherein it is seen that if a portion $M_1$ which repeats at a certain period T is shifted along the time axis by an interval of time which is equal to the period T, the portion $M_1$ will be superimposed on the immediately succeeding portion $M_2$ with maximum accuracy.

In order to obtain the autocorrelation function from the biosignal, we may write the autocorrelation function $A(\tau)$ in terms of the biosignal f(t) which is a function of the time t. Thus, A(T) may be written $$A(\tau) = \lim_{T \to \infty} \frac{1}{2T} \int_{-T}^{T} f(t)f(t + \tau)dt \quad (1)$$

in which T represents the period of the biosignal and $\tau$ represents a time interval between two points in time separated by a given interval, the earlier point in time being a reference time in connection with the biosignal. In other words, $\tau$ is a variable which applies a phase difference to the biosignal f(t) along the time axis.

Reference will now be had to FIG. 2 to describe the conventional period measurement system that relies upon the correlation function to measure the period of a biosignal, specifically a signal representative of the heartbeat of a fetus, which signal will be referred to as a "heartbeat signal" hereafter.

In FIG. 2, a probe 2 is brought into contact with, say, the abdomen of a female subject to extract the fetal heartbeat signal for the purpose of measurement. The heartbeat signal so detected has its waveform suitably processed in a preprocessing circuit 3 and then sampled at a predetermined sampling period in a sampling circuit 4. The data obtained by sampling the heartbeat signal is stored in a data memory 6 composed of a plurality of shift registers. As each item of new data enters the data memory 6, items of data already stored up to that point are shifted to the immediately adjacent register, so that data is shifted sequentially from one register to another, with the oldest item of data in the last register being lost as each new input arrives. A multiplier 8 and an adder 10 constitute an autocorrelation function computing circuit which is adapted to compute an autocorrelation function using the data stored in the data memory 6. A correlation memory 12 stores the results of the computation, namely the computed autocorrelation function. Thus the autocorrelation function is computed by the multiplier 8 and the adder 10 on the basis of the data stored in the data memory 6. The computation is performed on the basis of single sampling-cycle divisions and, for each item of data $X_1, X_2, X_3 \ldots$, proceeds in the manner $X_1 \cdot X_{s+1} + A_1 \to A_1, X_1 \cdot X_{s+2} + A_2 \to A_2, \ldots, X_1 \cdot X_{s+m} + A_m \to A_m$, the result of each computation being stored sequentially in the correlation memory 12. By repeating these computation and storage operations for n cycles, data defining the autocorrelation function is stored in the correlation memory 12. Peaks representing the periodicity of the autocorrelation function stored in the correlation memory 12 are detected by a peak detector 14 in order to obtain the period of the biosignal.

In the conventional measurement system of the type described, however, the arrangement is such that the phase difference variable $\tau$ is varied in each single sampling cycle. It is therefore necessary to store in the correlation memory 12 the results of each and every autocorrelation function computation covering the entire body of data spanning the range over which the variable $\tau$ is varied in each sampling cycle. This means that the correlation memory must have a very large storage capacity. In addition, even when measuring a signal having a short period the computations described above are performed over a time interval corresponding to from two to three times the length of the period, so that much of this computation is without substantial meaning. This fact also calls for a correlation memory of a large storage capacity and is also disadvantageous when viewed in terms of real-time processing owing to the fact that a large number of substantially meaningless computations are performed.

SUMMARY OF THE INVENTION

Accordingly, it is an object of the present invention to provide a system for measuring the period of a biosignal, which system is free of the aforementioned defects so that it may enable period measurement with a correlation memory of a smaller storage capacity and with a computation time period that is shortened to the maximum possible extent.

Another object of the present invention is to provide a period measurement system that enables correct measurement of the period by detecting true peaks, which correspond to the period of a biosignal, from a plurality of peaks obtained from an autocorrelation function.

To these ends, the present invention provides a period measurement system comprising means for extracting a biosignal, autocorrelation function computation means for computing an autocorrelation function of the biosignal, peak detection means for detecting a peak from the autocorrelation functions, and period computation means for computing the period of the biosignal from that position on a correlation axis at which a peak is detected by the peak detection means, the computation of the autocorrelation function being continued for an interval corresponding essentially to the minimum value of the period of measurement, which interval begins with the detection of a peak, it being confirmed that no peak larger than the detected peak exists in the interval which corresponds to the minimum value and which begins with the detection of the peak, so as to detect that said peak is a true peak. In another aspect of the invention, the autocorrelation function, given by the equation $$A(\tau) = \frac{1}{n} \sum_{k=1}^{n} f(k) \cdot f(k+\tau)$$

for a certain value of a variable $\tau$ that applies a phase difference to the biosignal on the time axis, is computed in the autocorrelation function computation means for a specific value of the phase difference variable $\tau$, the specific value of the phase difference variable $\tau$ is advanced on the time axis to conform to the progress of the sampling cycles, whereby the autocorrelation function computation means computes autocorrelation functions one after another corresponding to the new specific values of the phase difference variable, and the computed value of the autocorrelation function is stored in memory and compared to the most recent computed value of an autocorrelation function, so as to detect a peak.

BRIEF DESCRIPTION OF THE DRAWINGS

FIG. 4 is a fetal heartbeat signal waveform diagram useful in describing a case where the period measurement signal of the present invention is appplied to measurement of the period between fetal heartbeats;

FIG. 5 is a waveform diagram useful in describing a system adapted to continue autocorrelation function computation for a fixed period of time following detection of a peak for the purpose of confirming whether or not the detected peak is a true peak;

FIG. 7 is a block diagram useful in describing the storing of sampling data in a data memory, as well as the reading and later processing of the data;

FIG. 8 is a block diagram showing the detailed construction of a peak detector, peak level checking circuit and peak confirmation circuit included in the period measurement apparatus shown in FIG. 6; and FIG. 9 is a block diagram useful in describing the details of a reference level generator.

DESCRIPTION OF THE PREFERRED EMBODIMENT

Figure 1:
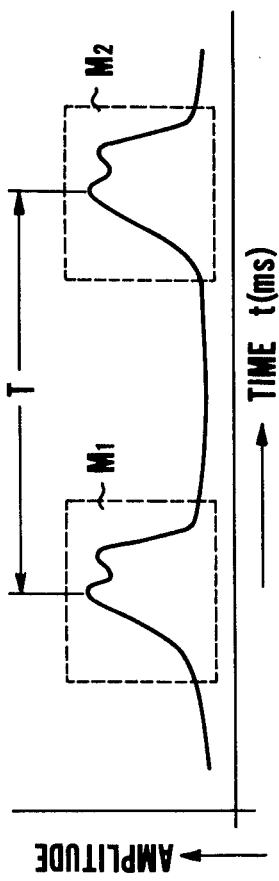
FIG. 1 is a biosignal waveform diagram useful in describing measurement of a period by means of an autocorrelation system.
Figure 3:
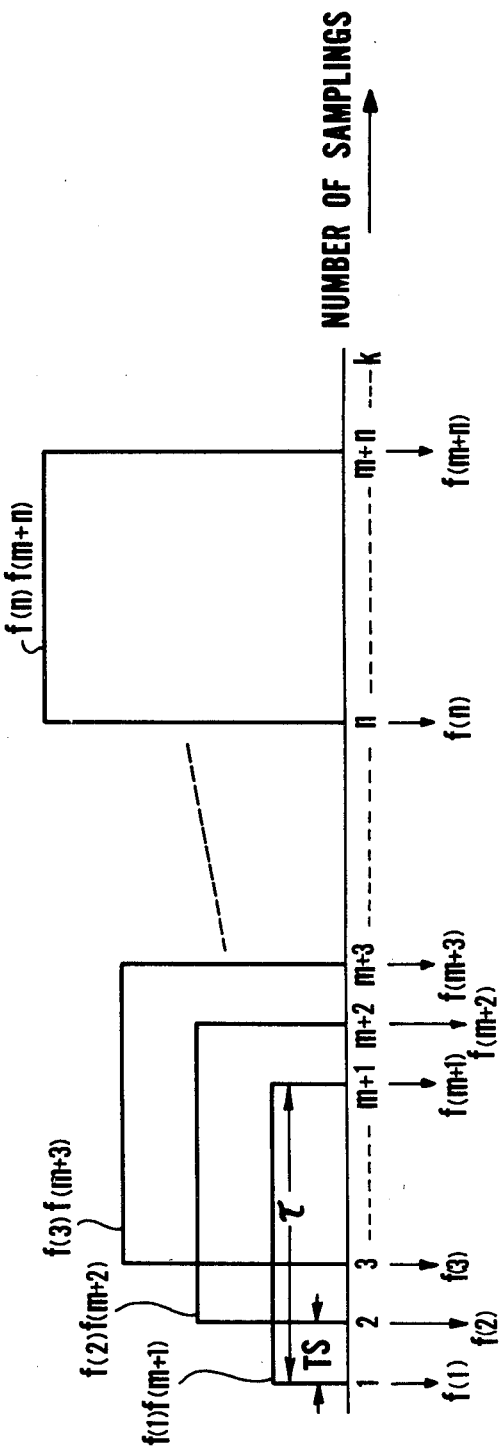
FIG. 3 is an illustrative view useful in describing the manner in which an autocorrelation function is computed in a period measurement system according to the present invention.
Figure 2:
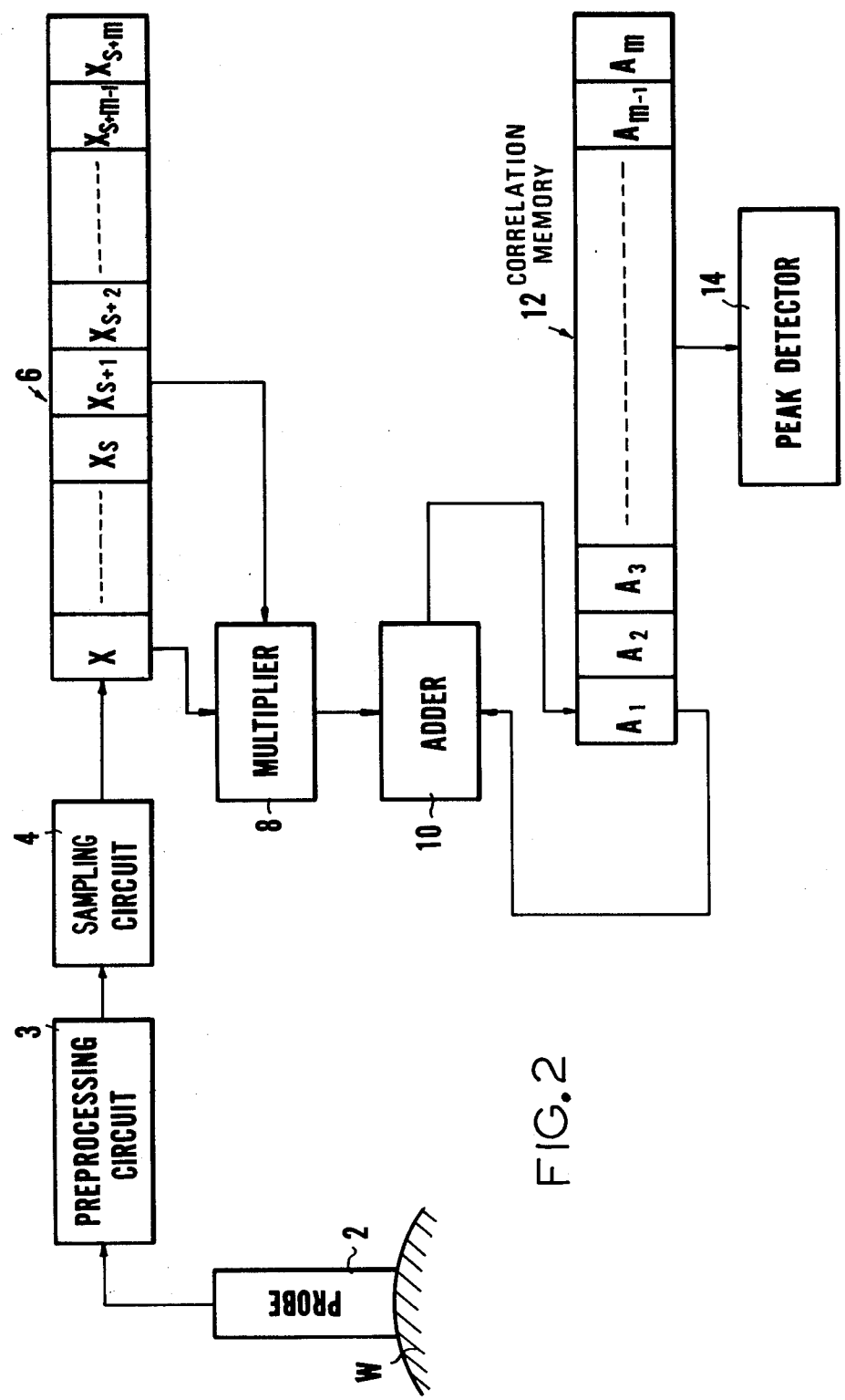
FIG. 2 is a block diagram showing, in simplified form, the construction of period measuring apparatus to which the conventional system of period measurement is applied.

FIG. 3 is useful in describing a period measurement system in accordance with the present invention, and illustrates the system employed in computing the autocorrelation function of a biosignal.

If we let f(k) (where k = 1, 2, 3, ..., n) denote the data obtained by respective sampling operations applied to a biosignal at a fixed sampling period $T_s$, then the autocorrelation function $A(\tau)$ of the biosignal will be expressed by equation (2), $$A(\tau) = \frac{1}{n} \sum_{k=1}^{n} f(k) \cdot f(k+\tau) \qquad 2)$$

in which $\tau$ stands for a variable that applies a phase difference to the biosignal along the time axis, n stands for the total number of multiplications or additions in one sampling cycle, and k stands for a sampling ordinal number. Expanding equation (2) gives us $$A(\tau)=1/n\{f(1)f(1+\tau)+f(2)f(2+\tau)+f(3)f(3+\tau)+\ldots +f(n)f(n+\tau)\} \qquad 3)$$

In equation (3), f(1) represents the most recent data. Equation (3) means that the autocorrelation function of a biosignal is found by summing the product $f(k)f(k+\tau)$ a total of n times by changing k, where $f(k)f(k+\tau)$ is the product of sampled data f(k) and $f(k+\tau)$ at two points in time separated by the phase difference variable $\tau$ along the time axis.

More specifically with reference to FIG. 3, assume that plural items of data are acquired by sampling operations conducted at intervals equal to the sampling period $T_s$ shown along the time axis, and that the phase difference variable $\tau$ is given by m. To compute the autocorrelation function A(m), two items of sampling data displaced from each other by m, such as f(1) and f(m+1), f(2) and f(m+2), f(n) and f(m+n) ..., are multiplied to give the products f(1)f(m+1), f(2)f(m+2) ... f(n)f(m+n). These products are then added together for the n sampling operations in the sampling cycle to give the autocorrelation function A(m). The system adopted in the present invention computes an autocorrelation function for a certain value of the variable $\tau$, which applies the phase difference to the biosignal on the time axis in one sampling cycle of the biosignal, changes the value of the phase difference variable $\tau$ along the time axis in conformance with the progress of the sampling cycles, and then computes an autocorrelation function which corresponds to each sampling cycle. The results of the most recent autocorrelation function computation is stored in memory, whereby the signal peaks and signal period can be found.

This will now be described in greater detail taking as an example a case in which the invention is applied to the period measurement of a fetal heartbeat signal.

The period of a fetal heartbeat ranges from approximately 300 to 1,500 milliseconds. Therefore, to compute an autocorrelation function over the range of the entire period of the heartbeat signal, it is necessary to find the autocorrelation function by varying the period of measurement from the minimum value of 300 milliseconds to the value of 1,500 milliseconds. In other words, it is necessary to change the phase difference variable $\tau$ over the range of $300/T_s$ to $1,500/T_s$ in equation (2). Since the autocorrelation function will have a maximum peak within this range when the phase difference variable $\tau$ is set to the heartbeat signal period T, or to a period of time which is an interval multiple of the period T, the true period of the heartbeat signal can be found if the peak corresponding to the period $\tau$ is detected.

In accordance with the period measurement system of the present invention, the autocorrelation function computation is performed with each sampling cycle serving as a single division. Ordinarily, the shortest period of a fetal heartbeat signal is approximately 300 milliseconds. As will become clear from the explanation given below, the ccomputation of the autocorrelation function starts from the smallest possible value of the period of measurement, namely 300 milliseconds, in order to extract the results of measurement over a time interval which is equivalent to the period. That is, in the first sampling cycle, the autocorrelation function is first found with regard to the interval of 300 milliseconds corresponding to the minimum value of the fetal heartbeat period. In this case the phase difference variable $\tau$ is found from $\tau = 300/T_s$, so that the variable $\tau$ will be 60 if we set the sampling period $T_s$ to five milliseconds. Then, with a sampling period $T_s$ of five milliseconds, the time permitted for a computation concerning the sampled data will be within about five milliseconds. Hence, n sampling operations are carried out under the conditions $\tau = 60$ and sampling period $T_s = 5$ milliseconds, and the autocorrelation function $A(60)$ is found for $\tau = 60$. The autocorrelation function $A(60)$ is found by the method used to find the autocorrelation function $A(\tau)$ in FIG. 3.

The foregoing will now be described with reference to FIG. 4 which shows a heartbeat signal. Sampling is conducted up to a total of n times at intervals of five milliseconds, which is equal to the sampling period $T_s$ (i.e., at intervals defined by $T_s = 5$ milliseconds). Items of data $f(1)$, $f(2)$, $f(3)$, $f(4)$ ... $f(n)$ obtained by each sampling operation are stored in memory. Next, two items of data $f(k)$ and $f(k+60)$ obtained at two different sampling times displaced from each other by the phase difference variable $\tau = 60$ are multiplied together, and a series of these products, such as $f(1)f(1+60)$, $f(2)f(2+60)$ ... are added together to give the sum of the products. Thus, it is possible to find the autocorrelation function $A(60)$ for the case in which the phase difference variable $\tau$ is set to 60. The value of $A(60)$ indicates the degree of periodicity in connection with $\tau = 60$ (i.e., for a period of 300 milliseconds). The value of $A(60)$ is stored in memory for the purpose of comparison until the autocorrelation function is obtained in the next sampling cycle.

Next, the computation is performed for the second sampling cycle, wherein the value of the phase difference variable is advanced by one to $A(61)$. In other words, in the second sampling cycle the autocorrelation function is computed for a period of 305 milliseconds. The computation of the autocorrelation function $A(61)$ is carred out in essentially the same manner as the computation of the autocorrelation function $A(60)$ and is not described again here. The autocorrelation function $A(61)$ obtained from the computation for the period of 305 milliseconds is compared with the autocorrelation function $A(60)$ for the period of 300 milliseconds, as previously computed and stored in memory. Thus, the system adapted herein computes an autocorrelation function for a certain value of the phase difference variable $\tau$ in one sampling cycle, stores in memory solely the result of this computation, and then compares this result with the result of an autocorrelation function computation for a phase difference variable whose value is advanced by one count in the next sampling cycle. According, only the result of the autocorrelation function computation in the most recent cycle need be stored in memory. The system of the present invention therefore makes it possible to reduce the required memory capacity of the correlation memory in comparison with the conventional system which requires that the correlation memory stores the results of each and every autocorrelation function computation covering the entire body of data spanning the range over which the phase difference variable $\tau$ is varied in each sampling cycle.

In order to detect the signal peaks in accordance with the present invention, the value which has previously been computed and stored for the preceding sampling cycle is compared with the value computed for the next sampling cycle. The signal peaks are then detected by repeating this comparison process and examining the change in state. When there is a change in state from a larger value to a smaller value between two continuous sampling cycles, this indicates the detection of a peak in the first of the two cycles. In effecting the peak detection operation, the comparison is made solely with the immediately preceeding computed value, in accordance with the description given above. However, it is obviously also possible to store computed values relating to several cycles and to perform a comparison among these values if desired.

In the embodiment described above a microprocessor can be employed owing to the reduction in the required storage capacity and the reduction in the number of computations. It therefore becomes possible to effect highly accurate autocorrelation function computations and system control. However, it should be noted that the foregoing operation unfortunately detects not only an intrinsic peak corresponding to the signal period, but other peaks that generally tend to exist in the vicinity of the intrinsic peak. Therefore, in order to measure the period with a high order of precision, means must be provided to detect the intrinsic or true peak, which corresponds to the signal period, from among the several peaks that may exist.

In order to determine whether a detected peak has the potential of being a true peak, two steps are required. First, a level check operation is performed on the basis of a minimum level determined to serve as a threshold value, and second, when a peak has been detected, the autocorrelation function computation is continued for a length of time which corresponds to the smallest period of measurement, to confirm that no peak larger than the detected peak exists in the interval over which the computation has been continued. These two steps enable the detection of a true peak.

The level check operation comprises the steps of determining the threshold value of a level used in judging whether a peak has the potential of being a true peak, and then judging whether the level of a peak exceeds the threshold value, whereby it is decided whether the detected peak, which has the potential of being a true peak, should indeed be regarded as a true peak.

In the example of this embodiment, the threshold value is set to one-half the value of a peak employed in an immediately preceding measurement, namely to one-half the value of the most recent true peak, and only the peak whose level exceeds the set threshold value is judged to be a peak which has the potential of being a true peak.

The threshold value need not necessarily be set to one-half the value of the most recent true peak, but should be set to the optimum value chosen in accordance with the condition of the signal at that time. In general though the peak value of the true peak that indicates the period of the signal is influenced by the strength and waveform of the signal, noise poses a particular problem. Specifically, the lower the noise the larger and more distinct the true peaks present themselves, whereas the greater the noise the smaller the true peaks appear. In fact, the value of a true peak in the presence of considerable noise may even be smaller than a false peak in the vicinity of a true peak when there is little noise.

It is for this reason that the threshold value must be set in accordance with the signal conditions that exist during peak detection. In this embodiment, in addition to the level check described above, the autocorrelation function computation is continued for a fixed interval of time following the detection of a peak, and a check is performed to determined whether a peak larger than the detected one exists within said fixed interval.

It has been stated above that peaks obtained from an autocorrelation function include, in addition to a true peak that corresponds to the signal period, several peaks located in the vicinity of the true peak. The true peak must be detected among the several peaks in order to measure the period correctly. Since the peaks in the vicinity of the true peak are generally located quite close to the true peak, it is possible to prevent the former peaks from being detected as the true peak by prolonging the autocorrelation function computation for a fixed interval following the detection of a peak and then by checking whether a peak larger than the detected one exists within said fixed interval. It should be noted that it is sufficient if the fixed interval is set to an interval of a value corresponding to the minimum period of measurement. Accordingly, in this embodiment, once a peak has been detected the computation of the autocorrelation function is prolonged for an interval that corresponds essentially to the minimum value of the period of measurement, namely to 300 milliseconds.

The foregoing will be described in connection with FIG. 5. If we assume that peak $P_1$ is detected at time $t_{11}$ (present time), the computation of the autocorrelation function will be continued for 300 milliseconds after time $t_{11}$, namely until time $t_{12}$. As FIG. 5 shows, a peak $P_2$ larger than peak $P_1$ is detected at time $t_{21}$ in the 300-millisecond interval between time $t_{11}$ and time $t_{12}$. Under such condition, peak $P_1$ is discarded and the autocorrelation function computation is continued for another 300 milliseconds starting from the new peak $P_2$, that is, until time $t_{22}$. Peak $P_2$ is detected as the true peak when no peak larger than $P_2$ is found to exist in the latter 300-millisecond interval. It will be noted in FIG. 5 that a peak $P_3$, of a smaller amplitude than peak $P_2$, is found at a certain time $t_{31}$ within the 300-millisecond interval between the time $t_{12}$ at which $P_2$ is detected, and time $t_{22}$. However, the peak $P_3$, whose amplitude is smaller than that of peak $P_2$, is not detected as a peak having the potential of being a true peak. Thus, the peak $P_2$ obtained at time $t_{21}$ is detected as being a true peak indicative of the period when 300 milliseconds have passed starting from time $t_{21}$, that is, when time $t_{22}$ has been reached. At this point in time the autocorrelation function computation ends and the period is calculated. The value of the phase difference variable $\tau$ of the true peak found in this manner corresponds to the period. Letting $T_s$ be the data sampling period, the period T is found from the computation formula $T = \tau \times T_s$. The next period measurement again starts from $\tau = 60$ (corresponding to the period of 300 milliseconds) and proceeds in the same manner.

Thus, the correct period of the biosignal is measured in the manner described above.

In the above, the fact that autocorrelation function starts from 300 milliseconds on the autocorrelation ($\tau$) axis and ends at a point equivalent to the biosignal period T+300 milliseconds, is extremely important in terms of true peak detection and the point in time at which the results of measurement are delivered as an output.

First, with regard to true peak detection, a true peak cannot exist below the shortest possible period of the biosignal undergoing measurement, and a true peak also cannot exist in an interval within the shortest period. Therefore, peaks which are confirmed in this manner can be said to be those which have absolutely no possibility of indicating peaks of a period which is twice the true period.

In connection with the output timing of the results of measurement, the effect of the arrangement mentioned above is to enable the results of measurement to be delivered in synchronism with the true period of the biosignal. More specifically, period measurement starts from 300 milliseconds, which is the short possible period. On the other hand, 300 milliseconds, equivalent to the shortest possible period, is set as the true peak confirmation interval, so that the results of measurement can consequently be delivered in a time interval which is equivalent to the true period of the biosignal. For example, if the true period is 500 milliseconds, the results of measurement will be output every 500 milliseconds. When the period change the output intervals change correspondingly. This is because the autocorrelation function computation proceeds at real-time on the correlation axis if the autocorrelation function computation interval coincides with the data sampling period, that is, because the correlation computation, for a length of time from the shortest period of the biosignal until a time represented by the sum of the shortest period and the true period, is performed within a time equivalent to the true period of the biosignal.

Figure 6:
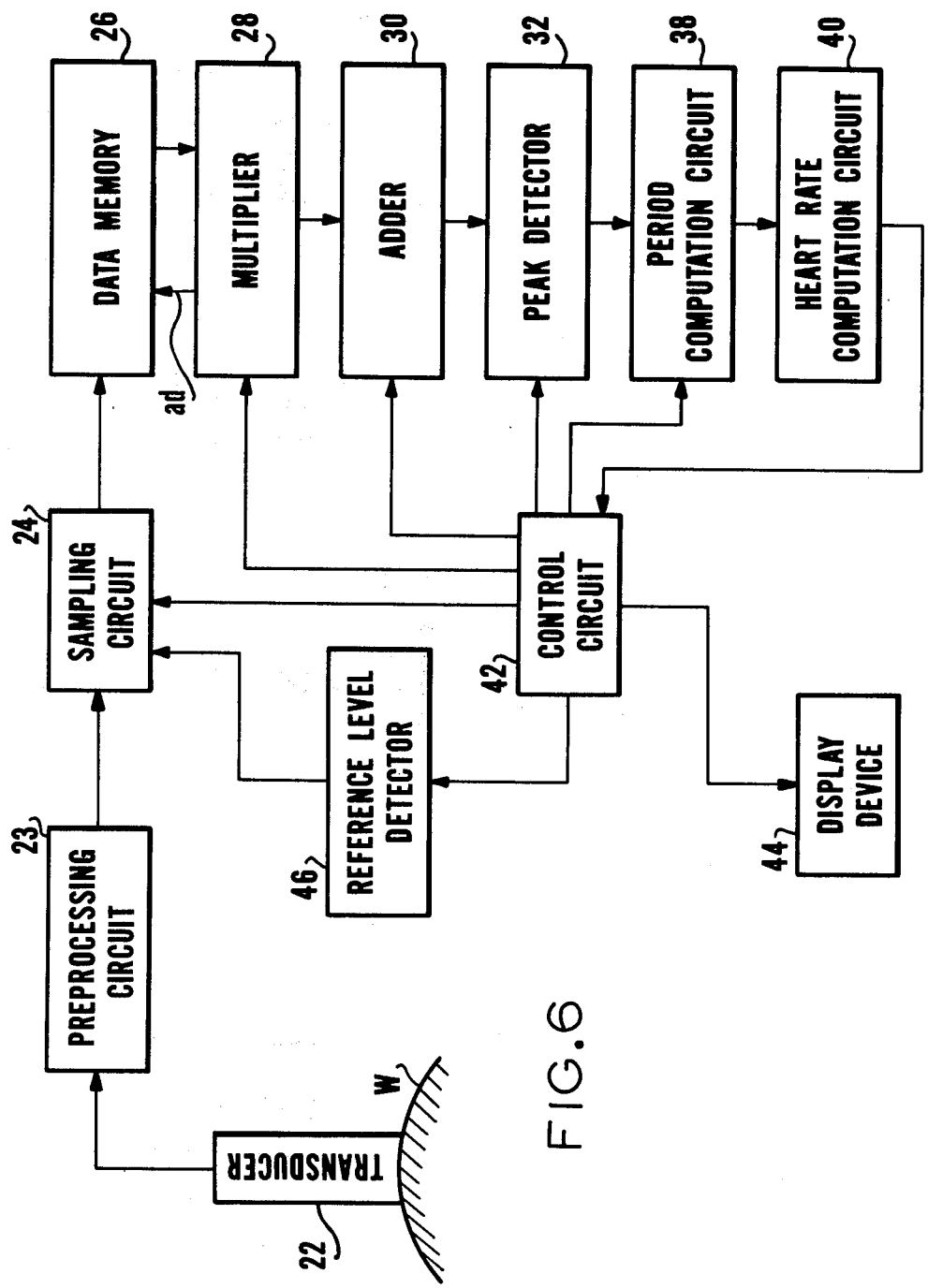
FIG. 6 is a block diagram showing, in simplified form, the construction of a period measurement apparatus to which the period measurement system of the present invention is applied.

FIG. 6 shows, in simplified form, the construction of a period measurement apparatus for practicing the period measurement system described above in connection with FIGS. 3 through 5.

With reference now to FIG. 6, a transducer is brought into contact with the abdomen W of a female subject in order to detect the fetal heartbeat signal. A sampling circuit 24 is connected to the transducer 22 through a preprocessing circuit 23. The heartbeat signal detected by the transducer 22, after having its waveform suitably shaped by the preprocessing circuit 23, is sampled by the sampling circuit 24 at a predetermined sampling period and is subjected to an analog-to-digital conversion (AD conversion) by the sampling circuit. The heartbeat signal therefore emerges from the sampling circuit 24 as a digital signal. A data memory 26 is connected to the sampling circuit 24 and stores the sampled data obtained from the sampling circuit. The data memory 26 is composed of a plurality of shift registers and operates as follows. As each new item of data enters the data memory, items of data already stored up to that point are shifted byte-to-byte, with the oldest item of data being lost as each new input arrives. A multiplier 28 is connected to the data memory 26, and an adder is connected to the multiplier 28. More specifically, the data memory 26 or shift register comprises a 1-byte (8-bit) parallel register which is adapted to "shift in" the sampled data in digital form. It is so constructed that arbitrary positional data specified by signal line ad can be read out therefrom. Included in the data memory 26 are a random access memory (RAM) with a read and write capability, and a controller for the RAM.

The multiplier 28 and an adder 30 constitute a computation circuit for computing the autocorrelation function. This circuit computes the autocorrelation function of a biosignal, namely the fetal heartbeat signal, by performing the computation specified essentially by equation (3) using the data stored in the data memory 26. In other words, the computation of an autocorrelation function is performed in connection with a phase difference variable $\tau$ of a certain value in each sampling cycle. To be more specific, two items of data, which represent two positions on the time axis separated from each other by the phase difference variable $\tau$, are produced by a control circuit 42 in a manner to be described later, and the two items of data are stored at two addresses in the memory section of the data memory 26 (the addresses giving the memory locations, which are indicated by the hatch marks in block 26 of FIG. 7). To compute the autocorrelation function, the two items of stored data are multiplied and the product is entered in an accumulator located in the adder 30. The number of multiplication operations for one phase difference variable $\tau$ is n in equation (3), as will readily be understood from the foregoing description, so that the number of additions is n. Completing n additions in effect computes the phase difference variable $\tau$ as a value which is n times the autocorrelation function. However, since n is constant, the data which is computed is proporational to the autocorrelation function in equation (3), so that, in essence, the autocorrelation function is calculated.

A peak detector 32 is connected to the adder 30 and is capable of storing a small quantity of data and of performing a comparison operation. An input to the peak detector 32 is the value of the autocorrelation function calculated by the computation circuit constructed by multiplier 28 and adder 30. The peak detector 32, as will be described in more detail later, stores the previously computed value of the autocorrelation function for one sampling cycle, and compares this value with the newly arrived computed value of the autocorrelation function for the next sampling cycle. The peak detector then stores the newly arrived computed value if it is larger than the previously stored computed value. Since the peak detector 32 need store only the computed value of the autocorrelation function for the most recent sampling cycle and the value of the phase difference variable $\tau$ at that time, a small memory capacity will suffice. Thus, the stored computed value for one sampling cycle is compared with the computed value of the autocorrelation function for the next sampling cycle by means of a comparator, thereby allowing the change in values for the two sampling cycles to be investigated. When the result of the comparison operation shows a transition from a higher to a lower value, this indicates the existence of a peak in the first of the two sampling cycles. The peak detector 32 performs a comparison between a peak detection signal and a reference level. In order to set the reference level, use may be made of a level which is, for example, one-half the previously measured true peak value, as described earlier. If the detected peak exceeds the reference level, and it is confirmed that no peak larger than the detected peak is present within a fixed time interval measured from the instant at which the detected peak exceeds the reference level (which fixed time interval is 300 milliseconds in this embodiment), then the peak detector 32 judges that the detected peak is a true peak and issues a true peak detection signal.

Connected to the peak detector 32 is a period computation circuit 38 which, upon receiving the true peak detection signal from a peak detector 32, computes the period on the basis of the value of the phase difference variable in the autocorrelation function at the time that the peak is obtained, said value being preserved in a register located within the peak detector.

Connected to the period computation circuit 38 is a heartbeat computation circuit 40 which computes the number of heartbeats on the basis of the period computed by the period computation circuit 38.

The heartbeat computation circuit 40 is connected to a control circuit 42, having a display device 44, such as an arrangement of light-emitting diodes (LED), connected thereto. The display device 44 displays the number of heartbeats in the heartbeat signal on the basis of the signal obtained from the heartbeat computation circut 40 through the control circuit 42. There may be occasions where the signal from the heartbeat computation circuit 40 includes a noise component, or where the probe for heartbeat detection slips. The control circuit 42 therefore is adapted to so control the signal from the heartbeat computation circuit 40 as to prevent it from entering the display device 44 on such occasions, thereby assuring that an erroneous heartbeat number will not be displayed.

The control circuit 42 is further adapted to deliver clock pulses to the sampling circuit 24, thereby to control the timing of the sampling operation effected by the sampling circuit. In addition, the control circuit sends the multiplier 28 a signal, indicative of the value of the phase difference variable, upon each sampling operation. The value of the phase difference variable successively advances as the sampling cycles progress, starting from a time which essentially corresponds to the minimum value of the hearbeat signal period. The multiplier 28 is adapted to read, from the data memory 26, two items of data separated by the value of the phase difference variable designated by the signal from the control circuit 42, and to find the product of the two items of data. The control circuit 42 sends a timing signal to the adder 30 which, on the basis of the timing signal, adds together the results of the computation operations executed by the multiplier 28. In other words, the multiplier 28 and adder 30, under the control of the control circuit 42, read data from the data memory and compute the autocorrelation function essentially as shown by equation (3).

Connected to the control circuit 42 is a reference level detector 46. The latter, in accordance with a timing signal delivered by the control circuit 42 at a suitable time interval, is adapted to detect the optimum reference level (zero level) for the purpose of attaching a positive (+) or negative (−) sign to the sampled data, and to send a signal indicative of the optimum reference level to the sampling circuit 24. In attaching the signs to the data, the more balanced the polarity of the data, the more reliable will be the periodicity of the autocorrelation function. The reference level detector 46 is provided for the purposes of finding the optimum value for achieving this end. Specifically, the detector 46 finds the optimum value of the reference level by detecting the maximum value and minimum value, or the average value, of the data during sampling.

The peak detector 32 may have the construction shown in FIG. 8. Here a memory 52 comprises two memory units, one for storing the value of the autocorrelation function, and the other for storing the value of the phase difference variable. More specifically, the memory 52, under the control of a write signal from a comparator 54, stores the value of the autocorrelation function computed by the adder 30, and the value of the phase difference variable obtained from the control circuit 42. The comparator 54 is adapted to compare the newly computed value of the autocorrelation function obtained from the adder 30 and the most recent, largest computed value of the autocorrelation function previously stored in the memory 52, and to deliver the write signal to the memory 52 if the newly computed value of the autocorrelation function is the larger of the two values, whereby the contents of the memory 52 are replaced by the newly computed value of the autocorrelation function and by the value of the phase difference variable obtained from the control circuit 42. When the value of the autocorrelation function changes from an increasing to a decreasing one upon repeating the aforesaid comparison operation, the comparator 54 judges that a peak has been detected and therefore issues a signal. The computed value of the autocorrelation function entered in the memory 52 is sent to a comparator 56 for checking the peak level. The comparator 56 compares this value with a reference level received from a reference level generator 58. The latter is set by the output timing of a counter 62 at such time that the preceding true peak is detected, whereby it stores a level equal to, say, one-half the value of the true peak detected by the preceding measurement. It is this level which the reference level generator delivers as the reference level. Obtaining one-half the value of a true peak is accomplished through the technique shown in FIG. 9. Specifically, this is accomplished by shifting the output data from the memory 52 one bit to the LSB (Least Significant Bit) side, and connecting the data to the comparator 56, which is a magnitude comparator. If the result of the comparison is such that the computed value of the autocorrelation function stored in the memory 52 is of a level that exceeds the reference level, the comparator 56 issues a signal. An AND gate 60 takes the logical product of the outputs from the comparators 54, 56. A positive-going transition in the output of the AND gate 60 resets the counter 62 and sets the value of the phase difference variable $\tau$, which has been stored in the memory 52, in a register 64. When the clock pulses being counted by the counter 62 reach a number which corresponds to a fixed time period, such as 300 milliseconds, the counter issues a signal. This output signal from the counter 62 indicates that a true peak has been detected, so that the value of $\tau$ which has been set in the register 64 is delivered to the period computation circuit 38. The latter circuit computes the period by taking the product of the variable $\tau$ and the sampling period arriving from the control circuit 42 on a signal line. By way of example, if the sampling period is five milliseconds and $\tau$ is 60 milliseconds, the period is computed as being 300 milliseconds. The obtained period is delivered to the heartbeat counter circuit 40 where the number of heartbeats for a period one minute is found by dividing $60 \times 10^3$ (ms) by the period (ms). The number of heartbeats found in this manner is then applied to control circuit 42 and displayed on the display device 44 under the control of the control circuit.

Thus, peaks are detected and checked through the foregoing arrangement and operation to assure the extraction of peaks that are true.

In accordance with the present invention as described above, measurement of a biosignal period is performed through the steps of computing an autocorrelation function for a certain value of the phase difference variable $\tau$ in one sampling cycle of the biosignal, changing the value of the phase difference variable $\tau$ on the time axis in conformance to the progress of the sampling cycles, computing an autocorrelation function in each sampling cycle, storing solely the result of the autocorrelation function computation for the initial cycle of two consecutive sampling cycles, comparing this result with the result of the autocorrelation function computation for the following cycle, and detecting a peak from the increase and decrease in the result of comparison, whereby the period of the biosignal is measured. Such an arrangement makes it possible to greatly reduce the storage capacity for the results of the autocorrelation function computations, and to eliminate meaningless autocorrelation computations for long intervals of time that may be two or three times as long as the actual biosignal period, thereby allowing data to be processed on an approximately real-time basis.

Furthermore, in accordance with another feature of the invention, the correct period can be measured through the steps of beginning the autocorrelation function computation essentially from the minimum value of the period of biosignal measurement, continuing the autocorrelation computation for an interval corresponding to said minimum value following the detection of a peak, and confirming that there is no peak larger than the initial peak in said interval corresponding to the minimum value measured from the point of initial peak detection, thereby to detect that the initial peak is a true peak. Thus it is possible to reliably detect solely a true peak which indicates the intrinsic period of the biosignal, thereby enabling measurement of the correct period. Moreover, since the range of autocorrelation function computation is restricted to an area from substantially the minimum value mentioned above to a range of values represented by the sum of the true biosignal period and confirmation interval (such as said minimum value), the invention has the effect of eliminating meaningless computations and of permitting real-time processing. In addition, the results of measurements can be delivered at a time interval which is equivalent to the period of the signal undergoing measurement.

As many apparently widely different embodiments of this invention may be made without departing from the spirit and scope thereof, it is to be understood that the invention is not limited to the specific embodiment thereof except as defined in the appended claims.

What we claim is:

1. A period measurement system for measuring the period of a biosignal, said period having a minimum value, comprising:
    data memory means for storing sampled input biosignal data and for shifting the stored biosignal data when new biosignal data is entered;
    autocorrelation function computation means for computing an autocorrelation function A $(\tau)$ of the sampled input biosignal data, given by the equation $$A(\tau) = \frac{1}{n} \sum_{k=1}^{n} f(k) \cdot f(k + \tau)$$

wherein a phase difference variable $\tau$ is specified over each computation cycle corresponding to k=1 to n, said variable $\tau$ being set to essentially the minimum value of the biosignal period being measured for an initial computation cycle, and thereafter incremented by a certain value in advance of each successive computation cycle of the autocorrelation function;

peak detection means for detecting a peak by comparing the autocorrelation function value previously computed by said function computation means with the autocorrelation function value most recently computed by said function computation means;

means for continuing the computation of the autocorrelation function for a fixed period of time following the detection by said peak detection means of a certain peak;

means for confirming that no peak larger than said certain peak exists in said fixed period of time, whereby said certain peak is determined to be a true peak; and period computation means for computing the period of the biosignal based on the phase difference variable for which a peak is detected by said peak detection means.

2. A period measurement system according to claim 1, in which said fixed period of time is set by said continuing means to essentially the minimum value of the period of the biosignal being measured wherein said period computation means computes the period of the biosignal within a time period which is substantially equivalent to the period of the biosignal.

3. A period measurement system for measuring the period of a biosignal, said period having a minimum value, comprising:

means for extracting a biosignal;

autocorrelation function computation means coupled to said extracting means for computing an autocorrelation function of the biosignal wherein said autocorrelation function varies according to position along a correlation axis;

peak detection means coupled to said function computation means for detecting peak from the autocorrelation function;

period computation means coupled to said peak detection means for computing a period of the biosignal from that position on the correlation axis at which a peak is detected by said peak detection means;

means for continuing the computation of the autocorrelation function for an interval corresponding essentially to the minimum value of the period of the measured signal, which interval begins with detection of a certain peak by said peak detection means; and means for confirming that no peak larger than said certain peak exists in said interval which corresponds to said minimum value and which begins with the detection of said certain peak, whereby said certain peak is determined to be a true peak.

4. A period measurement system according to claim 3, including means for setting a threshold value for detection of a peak by said peak detection means wherein the value of a determined true peak serves as a reference, said peak detection means detecting as peaks only those peaks that exceed the threshold value.

5. A method of measuring the period of a biosignal, comprising the steps of:

obtaining biosignal data corresponding to a biosignal the period of which is to be measured;

repeatedly computing an autocorrelation function of the biosignal data including setting a minimum phase difference, deriving pairs of values of the biosignal data by selecting the data according to the minimum phase difference, summing the products of the derived pairs of values thereby providing a computed output, and incrementally advancing the phase difference between the selected data for each successive computing step;

detecting a peak in the computed output provided by said computing step; and determining the period of the biosignal according to the total phase difference between the selected biosignal data for which a peak in the computed output is detected.

6. The method of claim 5, including continuing said computing step for a continued interval corresponding essentially to a minimum period of the biosignal being measured, starting said continuing step upon the detection of a peak in the computed output provided by said computing step, confirming that no peak larger than the detected peak exists in the continued interval thus determining that the detected peak is a true peak.

7. The method of claim 6, including establishing a threshold value for the detection of a peak in said detecting step, and basing the threshold value on the value of the determined true peak.

* * * * *